United States Patent
Shah et al.

(10) Patent No.: US 10,342,128 B2
(45) Date of Patent: Jul. 2, 2019

(54) DEPOSITING BULK OR MICRO-SCALE ELECTRODES

(71) Applicant: LAWRENCE LIVERMORE NATIONAL SECURITY, LLC, Livermore, CA (US)

(72) Inventors: Kedar G. Shah, San Francisco, CA (US); Satinderpall S. Pannu, Pleasanton, CA (US); Vanessa Tolosa, Oakland, CA (US); Angela C. Tooker, Dublin, CA (US); Heeral J. Sheth, Oakland, CA (US); Sarah H. Felix, Oakland, CA (US); Terri L. Delima, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 259 days.

(21) Appl. No.: 15/274,363

(22) Filed: Sep. 23, 2016

(65) Prior Publication Data
US 2017/0013713 A1 Jan. 12, 2017

Related U.S. Application Data

(62) Division of application No. 14/210,233, filed on Mar. 13, 2014, now Pat. No. 9,485,873.
(Continued)

(51) Int. Cl.
*H05K 1/11* (2006.01)
*H05K 3/40* (2006.01)
(Continued)

(52) U.S. Cl.
CPC ............ *H05K 1/11* (2013.01); *A61N 1/05* (2013.01); *A61N 1/0553* (2013.01); *H05K 1/09* (2013.01);
(Continued)

(58) Field of Classification Search
CPC ........ H05K 3/4007; H05K 3/007; H05K 3/12; H05K 3/20; H05K 3/28; H05K 1/11;
(Continued)

(56) References Cited

U.S. PATENT DOCUMENTS 3,006,067 A 10/1961 Anderson et al.
3,738,368 A * 6/1973 Avery ............... A61N 1/0553
607/117
(Continued)

OTHER PUBLICATIONS

Fomani et al., "Flexible Neural Microelectrode Arrays Reinvofced with Embedded Metallic Micro-Needles", 2010, IEEE Sensors 2010 Conference Publication, pp. 1601-1604.*
(Continued)

*Primary Examiner* — Peter Dungba Vo
*Assistant Examiner* — Jeffrey T Carley
(74) *Attorney, Agent, or Firm* — Eddie E. Scott

(57) ABSTRACT

Thicker electrodes are provided on microelectronic device using thermo-compression bonding. A thin-film electrical conducting layer forms electrical conduits and bulk depositing provides an electrode layer on the thin-film electrical conducting layer. An insulating polymer layer encapsulates the electrically thin-film electrical conducting layer and the electrode layer. Some of the insulating layer is removed to expose the electrode layer.

7 Claims, 3 Drawing Sheets

Related U.S. Application Data

(60) Provisional application No. 61/801,370, filed on Mar. 15, 2013.

(51) Int. Cl.
*A61N 1/05* (2006.01)
*H05K 1/09* (2006.01)
*H05K 3/12* (2006.01)
*H05K 3/20* (2006.01)
*H05K 3/28* (2006.01)
*H05K 3/00* (2006.01)

(52) U.S. Cl.
CPC ............... *H05K 1/097* (2013.01); *H05K 3/12* (2013.01); *H05K 3/20* (2013.01); *H05K 3/28* (2013.01); *H05K 3/4007* (2013.01); *H05K 3/007* (2013.01); *H05K 2201/0338* (2013.01); *H05K 2201/099* (2013.01); *Y10T 29/49147* (2015.01)

(58) Field of Classification Search
CPC .... H05K 1/09; H05K 1/097; Y10T 29/49147; A61N 1/05; A61N 1/0553
See application file for complete search history.

(56) References Cited

U.S. PATENT DOCUMENTS

| | | | |
|---|---|---|---|
| 2002/0142516 A1* | 10/2002 | Light | H01L 21/4853 438/107 |
| 2004/0140209 A1 | 7/2004 | Choi et al. | |
| 2006/0225274 A1 | 10/2006 | Greenberg et al. | |
| 2010/0200538 A1 | 8/2010 | Petisce et al. | |
| 2010/0305673 A1* | 12/2010 | Jolly | A61N 1/05 607/116 |
| 2010/0331935 A1* | 12/2010 | Tabada | A61N 1/05 607/116 |
| 2012/0190956 A1 | 7/2012 | Connolly | |

OTHER PUBLICATIONS

Felix et al., "Removable Silicon Insertion Stiffeners for Neural Probes Using Polyethylene Glycol as a Biodissolvable Adhesive," 34th Annual Int'l Conf. of the IEEE EMBS, 2012, pp. 871-887.

Shah et al., "Improved Chronic Neural Stimulation Using High Surface Area Platinum Electrodes," 35th Annual Int'l Conf. of the IEEE EMBS, 2013, pp. 1546-1549.

International Search Report and Written Opinion for PCT/US2014/030282 related to U.S. Appl. No. 14/210,233, 15 pages.

\* cited by examiner

DEPOSITING BULK OR MICRO-SCALE ELECTRODES

CROSS-REFERENCE TO RELATED APPLICATIONS

The present application is a Division of application Ser. No. 14/210,233 filed Mar. 13, 2014 entitled "depositing bulk or micro-scale electrodes", which claims benefit under 35 U.S.C. § 119(e) of U.S. Provisional Patent Application No. 61/801,370 filed Mar. 15, 2013 entitled "method for depositing bulk or micro-scale electrodes," the disclosure of which is hereby incorporated by reference in its entirety for all purposes.

STATEMENT AS TO RIGHTS TO APPLICATIONS MADE UNDER FEDERALLY SPONSORED RESEARCH AND DEVELOPMENT

The United States Government has rights in this application pursuant to Contract No. DE-AC52-07NA27344 between the United States Department of Energy and Lawrence Livermore National Security, LLC for the operation of Lawrence Livermore National Laboratory.

BACKGROUND

Field of Endeavor

The present application relates to microelectrodes and particularly to depositing bulk or micro-scale electrodes.

State of Technology

This section provides background information related to the present disclosure which is not necessarily prior art.

A large number of microelectronic devices utilize electrodes to make electrical contact with their environment. In large-scale devices, these electrodes can be fabricated from bulk materials. There is a large push to miniaturize such devices using microelectronics and MEMS technologies. For these devices, electrodes are deposited using physical-vapor deposition, chemical-vapor deposition, or electrochemical methods. For better performance of the microelectronic devices, it is often necessary to have a minimum electrode thickness, which is difficult to achieve reliably using conventional processes. Applicant has developed a system for attaching thicker electrodes on microelectronic (or large-scale) devices using thermo-compression bonding. This system permits reliable assembly of electrodes of various sizes. Additionally, this method reduces the number of fabrication steps (and potentially, cost) because the electrodes of desired shape and size are deposited, and hence require no further patterning or shaping.

Referring now to the drawings and in particular to FIG. 1, a prior art device is illustrated. The prior art device is designated generally by the reference numeral 100. The prior art device 100 has a thin body structure 102 that is adapted to be implanted in the anatomy of a human or animal. A number of sensor electrodes 104a, 104b, 104c, and 104d are imbedded in the thin body structure 102 such that the electrodes will be positioned in the desired position when the device is installed. Lead traces/wires, generally designated by the reference characters 106a, 106b, 106c, and 106d are electrically coupled to the electrodes 104a, 104b, 104c, and 104d respectively. The lead traces/wires are bundled together in a wire bundle 108 that includes contacts 110a, 110b, 110c, and 110d for connection to data collection and analysis equipment.

The prior art device 100 has a series of thin-film metal layers (forming electrodes and traces/wires) that are sandwiched between two insulating layers, such as polyimide or parylene. The areas above electrodes are opened to expose the electrodes to their environment. The sensor electrodes 104a, 104b, 104c, and 104d are generally of a large size compared to microelectronics and MEMS technologies devices. An example of a prior art device is illustrated in U.S. Pat. No. 3,738,368 for implantable electrodes for the stimulation of the sciatic nerve. U.S. Pat. No. 3,738,368 contains the description of the prior art device reproduced below:

"The implant 14 comprising the present invention consists of two spacedly opposed strips 16 made of a relatively thin, inert plastic material such as dacron mesh reinforced with silicon rubber. A plurality of contact buttons or electrodes 18 are imbedded in each of the strips 16, in a manner to be described more fully hereinafter, and lead wires, generally designated by the reference character 20, are electrically coupled to the contact buttons. The leads 20 are positioned at an angle to the length of the strips 16 and are color coded by any suitable means such as colored suture thread or lumens."

"Each of the strips 16 is preferably molded with a central section 16a and two laterally positioned end sections 16b, the central section 16a being in a plane different from the end sections 16b so that when the two strips 16 are positioned such as shown in FIG. 2, there will be a central recess for the nerve, the recess being defined by the spacedly opposed central sections 16a. The degree of molded-in curvature will depend upon the thickness of the plastic and the degree to which it can be made to envelope a portion of the nerve. While the various sections have been shown as being relatively flat and joined by angular portions 16c it should be understood that the various sections may also be gentle curves."

"Turning now to FIG. 3, the construction of a typical strip 16 and the mounting of an electrode button 18 thereon will be described. A staple 22 is welded at 24 to the inside surface of the cup-shaped electrode button 18. A platinum lead wire 26 is welded to the staple 22 as shown by the reference character 28. A stainless steel lead wire 30 is then secured to the platinum lead wire 26 at junction 32. A length of plastic 34, preferably medical grade silicon or the like, encapsulates the combined lead wires 26 and 30."

The disclosure of U.S. Pat. No. 3,738,368 is incorporated herein in its entirety by this reference for all purposes.

Referring now to FIG. 2, another prior art device and method of fabrication is illustrated. This prior art device and method of fabrication is designated generally by the reference numeral 200. The prior art device is a microelectrode device that has a body structure 202 adapted to be implanted in the anatomy of a human or animal. A number of electrodes are imbedded in the body structure such that the electrodes 204 be positioned in the desired position when the device is installed. The electrode 204 imbedded in a multi-layer body structure 202 is shown in FIG. 2. Lead lines electrically couple the electrodes to data collection and analysis equipment. Lead wire or trace 206 is shown electrically coupling the electrode 204 to data collection and analysis equipment 208 through connector 210 and connector line 212.

An example of a prior art device and method of fabrication is illustrated in US. Published Patent Application No. 2010/0331935 for a rigid spine reinforced polymer microelectrode array probe and method of fabrication. U.S. Published Patent Application No. 2010/0331935 contains the description of the prior art device and method of fabrication reproduced below:

"Turning now to the drawings, FIG. 1 shows an exploded isometric view of a first exemplary embodiment of the spine-reinforced microelectrode array probe of the present invention, generally indicated at reference character 10. The probe is shown as a single shank probe, having two main components, (1) an elongated probe body 11 which has an electrically-insulating material construction enclosing a plurality of conductive lines (and therefore also characterizable as an insulating probe body, a polymeric probe body if insulating polymers are used, or a flexible probe body if elastomeric insulating materials are used), and (2) a rigid spine (also characterized as an insertion shank) 30. Both the probe body 11 and the rigid spine 30 have an elongated configuration extending between respective opposing ends. In particular, the probe body 11 has an insertion end 12 with a pointed insertion tip 13 and an opposite connector end 14, and the rigid spine 30 has an insertion end 31 with a pointed insertion tip 32 and an opposite base end 33. While a single shank probe is shown in FIG. 1 to illustrate the features of the present invention, the present invention may also be realized and implemented as multi-shank probes. For such multi-shank embodiments, it is appreciated that the shanks are typically arranged in parallel and connected to a common base. Furthermore, each probe shank may have one or more contacts or exposed electrodes or leads."

"Microelectrodes 15-19 are shown located along the probe body 11 suitably near the insertion end 12. In particular, the microelectrodes are shown exposed through a top surface 28 of the probe body 11. And leads 20 are formed at the connector end 14 of the probed body for connecting to a connector, such as a percutaneous connector (not shown). Connecting the leads 20 to the respective microelectrodes 15-19 are the conductive lines (not shown) also characterized as wire traces. FIG. 2 is a cross-sectional view taken along the line 2-2 in FIG. 1 illustrating the thin film construction of the elongated probe body 11 and the particular electrical connection of microelectrode 15. As shown, two insulating layers 25 and 27 surround a conductive line, represented by bond pad 29. The electrode 15 is shown connected to the bond pad 29 and exposed at a top surface 28 through a via in the polymer layer 27. The microelectrode material may be, for example, activated iridium metal. And the spine 30 is shown spanning substantially the full length of the probe body, and illustrating the assembly and attachment of the separately fabricated components. As can be seen in FIG. 1 both the polymer probe body 11 and the rigid spine 30 were fabricated and released as separate components prior to being joined as shown. For the spine, foils of various thicknesses may be used, such as for example, 15, 25, or 50 um thick titanium foils."

"FIGS. 3 and 4 show the elongated probe body 11I and the rigid spine 30, subsequently joined and assembled together along an upper surface 34 of the spine and a lower surface 26 of the probe body. In particular, FIG. 3 is an isometric view of the embodiment of FIGS. 1 and 2 as assembled, and illustrating the fixed attachment of the pre-fabricated rigid spine 30, to the elongated probe body. And FIG. 4 is a cross-sectional view taken along the line 4-4 in FIG. 3 illustrating the thin film construction of the assembled microelectrode array probe through microelectrode 15. Preferably a bond or adhesive 36 is used to fixedly attach the two together. The adhesive may be either a type which produces a permanent bond, or a temporary one. For example, in one exemplary embodiment the adhesive used is a bio-adhesive (such as polysaccharide) of a type which loses its adhesion properties (e.g. dissolves) when placed in the body, so that the rigid spine only may be removed after insertion while the polymer probe body remains implanted."

The disclosure of US. Published Patent Application No. 2010/0331935 is incorporated herein in its entirety by this reference for all purposes.

SUMMARY

Features and advantages of the disclosed apparatus, systems, and methods will become apparent from the following description. Applicant is providing this description, which includes drawings and examples of specific embodiments, to give a broad representation of the apparatus, systems, and methods. Various changes and modifications within the spirit and scope of the application will become apparent to those skilled in the art from this description and by practice of the apparatus, systems, and methods. The scope of the apparatus, systems, and methods is not intended to be limited to the particular forms disclosed and the application covers all modifications, equivalents, and alternatives falling within the spirit and scope of the apparatus, systems, and methods as defined by the claims.

Applicant's apparatus, method, and systems provide a microelectrode device with a minimum electrode thickness, which can not be achieved reliably using conventional processes. The microelectrode device includes a device body having an underlying electrically insulating layer, a conductive thin-film layer on the underlying electrically insulating layer, and at least one electrode embedded in the electrically insulating layer wherein the at least one electrode is a bulk deposited electrode.

Applicant's method attaches thicker electrodes on microelectronic (or large-scale) devices using thermo-compression bonding. This method permits reliable assembly of electrodes of various sizes. Additionally, this method can reduce the number of fabrication steps (and potentially, cost) because the electrodes of desired shape and size are deposited, and hence require no further patterning or shaping. Applicant deposits a thin-film electrical conducting layer to form electrical conduits and bulk depositing an electrode layer on the thin-film electrical conducting layer. An insulating polymer layer encapsulates the electrically thin-film electrical conducting layer and the electrode layer. Some of the insulating layer is removed to expose the electrode layer.

The apparatus, systems, and methods for depositing bulk or micro-scale electrodes have use for medical devices (EEG, ECG, defibrillators, pacemakers, neural stimulators, neural recorders, etc.) and electrical/chemical sensors (glucose sensors, harsh environment, biochemical detection, etc.). For microelectronic devices, it is difficult to reliably deposit electrode materials with thicknesses greater than a few nanometers. Applicant's system for depositing bulk or micro-scale electrodes allows the deposition of extremely thick electrode materials with favorable electrical and mechanical properties. The system for depositing bulk or micro-scale electrodes can be applied to military and government sensor applications, where electrodes that can survive harsh environments for long periods of time are necessary.

The apparatus, systems, and methods are susceptible to modifications and alternative forms. Specific embodiments are shown by way of example. It is to be understood that the apparatus, systems, and methods are not limited to the particular forms disclosed. The apparatus, systems, and methods cover all modifications, equivalents, and alternatives falling within the spirit and scope of the application as defined by the claims.

BRIEF DESCRIPTION OF THE DRAWINGS

The accompanying drawings, which are incorporated into and constitute a part of the specification, illustrate specific embodiments of the apparatus, systems, and methods and, together with the general description given above, and the detailed description of the specific embodiments, serve to explain the principles of the apparatus, systems, and methods.

FIGS. 3A, 38, and 3C illustrate one embodiment of a method of fabric ating Applicant's microelectrode device.

DETAILED DESCRIPTION OF SPECIFIC EMBODIMENTS

Figure 1:
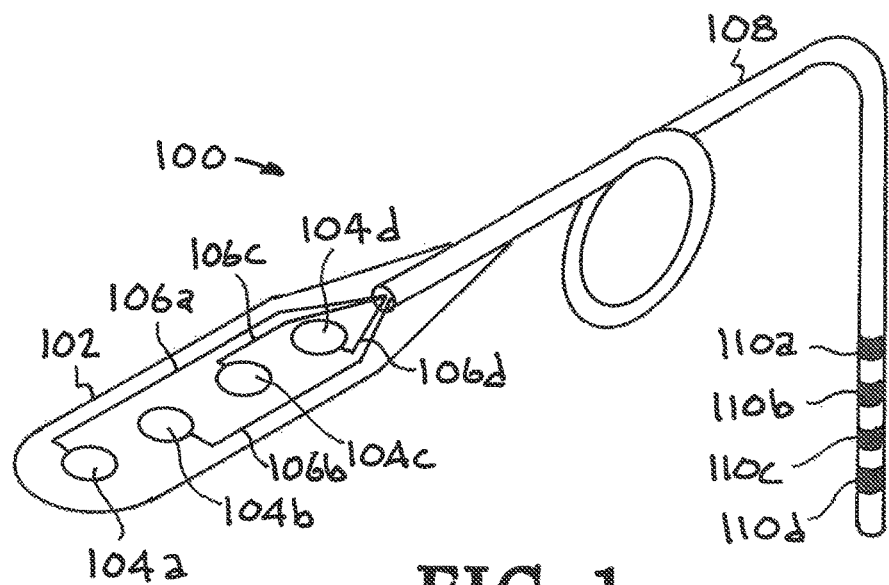
FIG. 1 illustrates a prior art device having electrodes and wires.
Figure 2:
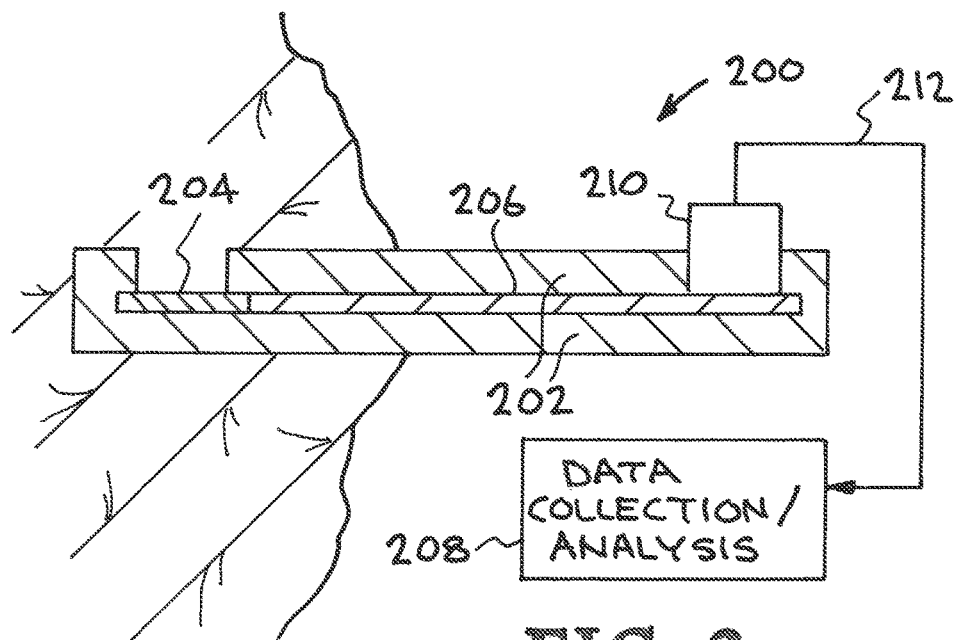
FIG. 2 illustrates a prior art microelectrode device with thin-film electrodes and wires.

Referring to the drawings, to the following detailed description, and to incorporated materials, detailed information about the apparatus, systems, and methods is provided including the description of specific embodiments. The detailed description serves to explain the principles of the apparatus, systems, and methods. The apparatus, systems, and methods are susceptible to modifications and alternative forms. The application is not limited to the particular forms disclosed. The application covers all modifications, equivalents, and alternatives falling within the spirit and scope of the apparatus, systems, and methods as defined by the claims.

It is often necessary to have a minimum electrode thickness, which is difficult to achieve reliably using conventional processes. Applicant presents a method of attaching thicker electrodes on microelectronic (or large-scale) devices using thermo-compression bonding. This method permits reliable assembly of electrodes of various sizes. Additionally, this method can reduce the number of fabrication steps (and potentially, cost) because the electrodes of desired shape and size are deposited, and hence require no further patterning or shaping.

Figure 3A:
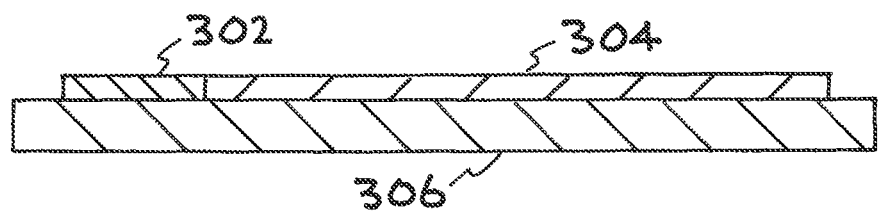
Figure 3B:
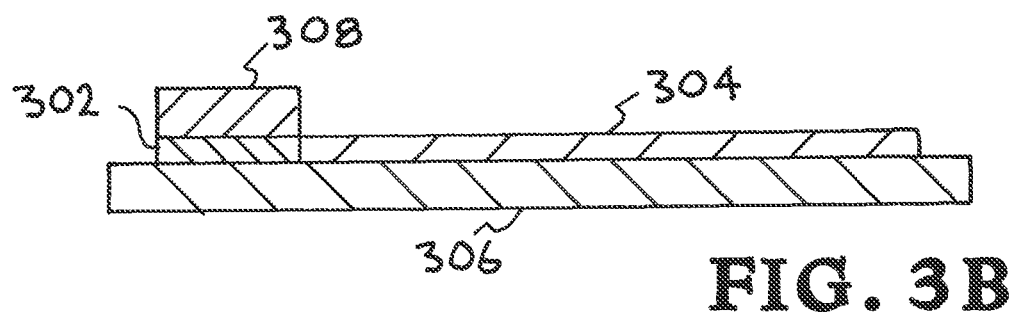
Figure 3C:
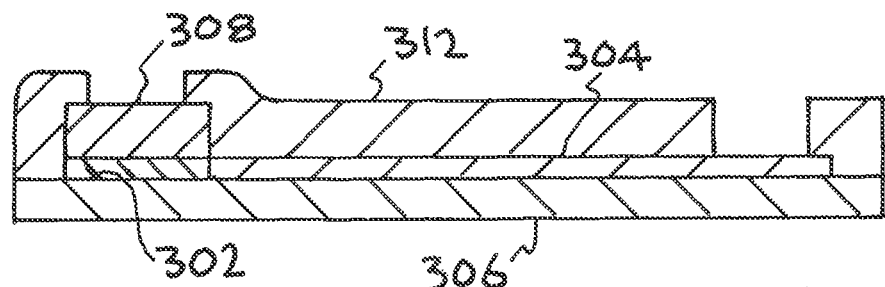

Referring now to FIG. 3A, FIG. 3B, and FIG. 3C; one embodiment of Applicant's implant device and method of fabricating the implant device is illustrated. A bulk electrode material consisting of metal thickness greater than 1 um is thermocompressively (heat/pressure) bonded to the bond pad to create a bulk electrode. Another insulator layer is deposited on top of the entire structure and an electrode opening is etched/created to expose the thick metal. In a similar fashion, the overall shape of the device is etched/created.

The method of fabricating the implant device includes various steps. First, as illustrated in FIG. 3A, a sensor element layer 302 and a trace metal layer 304 are deposited on a first polymer layer 306. Next, as illustrated in FIG. 3B, a thicker (bulk deposit) sensor layer 308 is deposited on the sensor element layer 302. The thicker (bulk deposit) sensor layer 308 is thermocompressively (heat/pressure) bonded to the sensor element layer 302 and bond pad to create a bulk electrode. Next, as illustrated in FIG. 3C, a second (top) polymer layer 312 is deposited on the thicker (bulk deposit) sensor layer 308, the sensor element layer 302, and the trace metal layer 304.

Figure 4A:
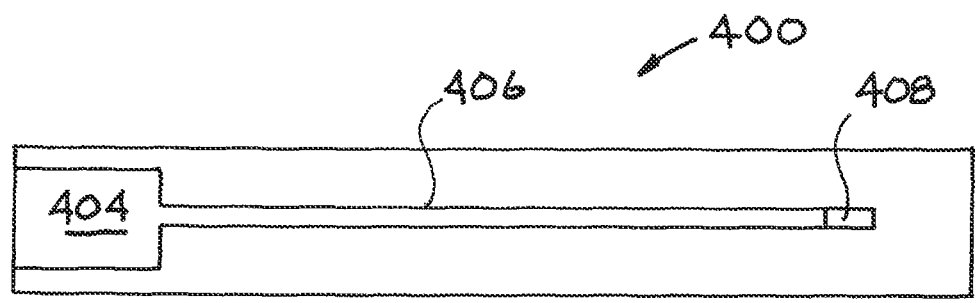
FIGS. 4A and 4B illustrate another embodiment of Applicant's microelectrode device and method of fabricating a microelectrode device.
Figure 4B:
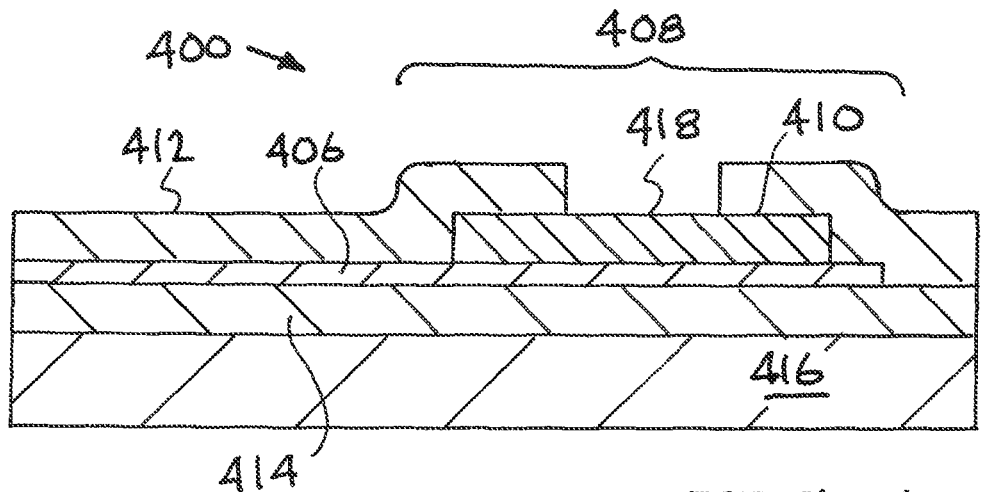

FIGS. 4A and 4B another embodiment of Applicant's microelectrode device and method of fabricating a microelectrode device are illustrated. A bulk electrode material consisting of metal thickness greater than 1 um is thermocompressively (heat/pressure/ultrasound) bonded to create a bulk electrode. An insulator layer is deposited on the entire structure and an electrode opening is etched/created to expose the thick metal.

FIGS. 4A and 4B show a cross section of a chip 400 where the electrode 402 has been 'bulk deposited' using thermocompression (combination of temperature, pressure, and ultrasonic energy). The chip 400 is shown in FIG. 4A as having a bond pad region 404, and electrical conduit, wire, or trace 406 and electrode region with exposed electrode material 408. A portion of the chip 400 and the method of fabricating the chip are illustrated in FIG. 4B.

The method of fabricating the implant device includes various steps. First, as illustrated in FIG. 4B, an insulating polymer layer 414 is deposited on a rigid substrate 416. Next, a conductive trace layer 406 is deposited on the insulating polymer layer 414. Next, a thicker bulk deposited electrode layer 410 is deposited on the conductive trace layer 406. The thicker bulk deposited electrode layer 410 is thermocompressively (heat/pressure/ultrasound) bonded to the conductive trace layer 410. Next, an insulating top polymer layer 412 is deposited on the deposited electrode layer 410 and the conductive trace layer 406. The electrode region 418 is then exposed. Finally the device is removed from the rigid substrate 416.

As explained and illustrated above, electrode materials (metals and non-metals) are deposited on a substrate using thermocompression bonding. Thermo-compression bonding is a process in which two materials are joined by bringing them in contact with an applied force at elevated temperature. The bonding temperature is below the eutectic melting temperature of the target/electrode material system. The mechanism for bonding is the inter-diffusion of the two materials, a process that is enhanced at elevated temperatures. Thermo-compression bonding is used for electrically connecting two electronics chips, or connecting an electronics chip to its package. In Applicant's device, system and method of fabrication; however, the thermo-compressively bonded material is the electrode itself.

The force and elevated temperatures can be applied with a flip-chip bonder. The tooling on the flip-chip bonder is made of a material that does not easily inter-diffuse with the electrode material. The electrode material is first aligned to the substrate, and then force and elevated temperatures are applied. For electrode materials that oxidize quickly, this process can be done in a vacuum or inert gas environment.

There are numerous advantages in thermo-compressively depositing electrodes of Applicant's device, system and method of fabrication. Some of the advantages are listed below.

Thicker electrodes—Electrodes of various thicknesses, especially thicker electrodes can be deposited without the stress and adhesion problems commonly seen in conventional PVD or electro-chemical deposition methods.

Reduction of process steps—Since a pre-shaped electrode can be bonded directly to the substrate, there is no need for lithographic patterning of the electrode material.

Three-dimensional electrode geometries—electrodes of various geometries can be deposited. Traditional deposition processes are inherently two-dimensional.

Wide scope of electrode materials—since the process is dependent on inter-diffusion, it is possible to deposit a wide variety of electrode materials that may not have developed processes for PVD or Electro-chemical deposition.

Process compatibility—Many traditionally deposited materials require specific etch chemistries to lithographically define them. These chemicals may not be compatible with the materials in the device. Thermo-compressively bonded electrodes do not need to be subjected to wet or dry etching processes.

Although the description above contains many details and specifics, these should not be construed as limiting the scope of the application but as merely providing illustrations of some of the presently preferred embodiments of the apparatus, systems, and methods. Other implementations, enhancements and variations can be made based on what is described and illustrated in this patent document. The features of the embodiments described herein may be combined in all possible combinations of methods, apparatus, modules, systems, and computer program products. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Therefore, it will be appreciated that the scope of the present application fully encompasses other embodiments which may become obvious to those skilled in the art. In the claims, reference to an element in the singular is not intended to mean "one and only one" unless explicitly so stated, but rather "one or more." All structural and functional equivalents to the elements of the above-described preferred embodiment that are known to those of ordinary skill in the art are expressly incorporated herein by reference and are intended to be encompassed by the present claims. Moreover, it is not necessary for a device to address each and every problem sought to be solved by the present apparatus, systems, and methods, for it to be encompassed by the present claims. Furthermore, no element or component in the present disclosure is intended to be dedicated to the public regardless of whether the element or component is explicitly recited in the claims. No claim element herein is to be construed under the provisions of 35 U.S.C. 112, sixth paragraph, unless the element is expressly recited using the phrase "means for."

While the apparatus, systems, and methods may be susceptible to various modifications and alternative forms, specific embodiments have been shown by way of example in the drawings and have been described in detail herein. However, it should be understood that the application is not intended to be limited to the particular forms disclosed. Rather, the application is to cover all modifications, equivalents, and alternatives falling within the spirit and scope of the application as defined by the following appended claims.

The invention claimed is:

1. A method of fabricating an implant device, comprising the steps of:
   depositing an electrically insulating polymer layer on a substrate,
   depositing a conductive trace layer on said electrically insulating polymer layer wherein said conductive trace layer has a trace layer thickness,
   depositing a bulk deposited electrode layer on a portion said conductive trace layer wherein said bulk deposited electrode layer has a bulk deposited electrode layer thickness and wherein said bulk deposited electrode layer thickness is thicker than said trace layer thickness,
   thermocompressively bonding said bulk deposited electrode layer to said portion of said conductive trace layer using heat, pressure, and ultrasound,
   depositing an encapsulating electrically insulating polymer layer on said conductive trace layer and said bulk deposited electrode layer,
   removing at least a portion of said encapsulating electrically insulating polymer layer that covers said bulk deposited electrode layer exposing at least a portion of said bulk deposited electrode layer,
   wherein the above steps produces the implant device, and
   releasing the implant device from said substrate.

2. The method of fabricating an implant device of claim 1 wherein said step of depositing a bulk deposited electrode layer on a portion of said conductive trace layer comprises depositing a bulk deposited metal electrode layer on a portion of said conductive trace layer.

3. The method of fabricating an implant device of claim 1 wherein said step of thermocompressively bonding said bulk deposited electrode layer to said portion of said conductive trace layer using heat, pressure, and ultrasound is accomplished using a combination of pressure and elevated temperature with ultrasonic energy to bond said bulk deposited electrode layer to said conductive trace layer.

4. The method of fabricating an implant device of claim 1 wherein said step of thermocompressively bonding said bulk deposited electrode layer to said portion of said conductive trace layer using heat, pressure, and ultrasound is accomplished using a flip-chip bonder, die bonder, or diffusion bonder.

5. The method of fabricating an implant device of claim 1 wherein said step of depositing a bulk deposited electrode layer on a portion of said conductive trace layer comprises depositing a bulk deposited platinum metal electrode layer on a portion of said conductive trace layer.

6. The method of fabricating an implant device of claim 1 wherein said step of depositing a bulk deposited electrode layer on a portion of said conductive trace layer comprises depositing a bulk deposited niobium metal electrode layer on a portion of said conductive trace layer.

7. The method of fabricating an implant device of claim 1 wherein said step of depositing a bulk deposited electrode layer on a portion of said conductive trace layer comprises depositing a bulk deposited iridium metal electrode layer on a portion of said conductive trace layer.

* * * * *